(12) United States Patent
Lim

(10) Patent No.: US 6,893,787 B2
(45) Date of Patent: May 17, 2005

(54) METHOD OF A PHOTOLITHOGRAPHY PROCESSING SYSTEM

(75) Inventor: Suing-Jun Lim, Suwon (KR)

(73) Assignee: Samsung Electronics Co., Ltd., Kyungki-do (KR)

( * ) Notice: Subject to any disclaimer, the term of this patent is extended or adjusted under 35 U.S.C. 154(b) by 0 days.

(21) Appl. No.: 10/809,857

(22) Filed: Mar. 26, 2004

(65) Prior Publication Data

US 2004/0184021 A1 Sep. 23, 2004

Related U.S. Application Data

(62) Division of application No. 10/178,306, filed on Jun. 25, 2002.

(30) Foreign Application Priority Data

Jul. 11, 2001 (KR) ........................................ 2001-41473

(51) Int. Cl.⁷ .............................. G03F 9/00; G03C 5/00
(52) U.S. Cl. .......................... 430/30; 430/311; 430/331
(58) Field of Search .......................... 430/30, 311, 331; 355/18, 40, 67; 356/237.1, 327.5

(56) References Cited

U.S. PATENT DOCUMENTS

| | | | | |
|---|---|---|---|---|
| 5,010,412 A | * | 4/1991 | Garriss | 348/371 |
| 6,407,809 B1 | * | 6/2002 | Finarov et al. | 356/237.3 |
| 6,721,045 B1 | * | 4/2004 | Hunter | 356/237.5 |
| 2002/0196336 A1 | * | 12/2002 | Batson et al. | 348/86 |

OTHER PUBLICATIONS

Copy of claims 1–23 from U.S. Appl. No. 09/680,226, filed Oct. 6, 2000.*

* cited by examiner

*Primary Examiner*—Christopher G. Young
(74) *Attorney, Agent, or Firm*—Lee, Sterba & Morse, P.C.

(57) ABSTRACT

A method of a photolithography processing system includes illuminating a surface of a wafer supported by a table with first illumination tools and a second illumination tool by positioning the first illumination tools at varying lateral heights relative to the table to illuminate the surface of the wafer at various predetermined angles of incidence and positioning the second illumination tool to illuminate the surface of the wafer vertically from above the wafer on the table, taking pictures of the surface of the wafer with a camera while the surface of the wafer is being illuminated, receiving a signal from the camera in a controller, detecting a presence of particles on the surface of the wafer with the controller, and transporting the wafer to the process-performing or cleaning position according to whether particles are detected on the surface of the wafer.

8 Claims, 4 Drawing Sheets

METHOD OF A PHOTOLITHOGRAPHY PROCESSING SYSTEM

This application is a DIVISION of application Ser. No. 10/178,306, filed Jun. 25, 2002.

BACKGROUND OF THE INVENTION

1. Field of the Invention

The present invention relates to a semiconductor device photolithography processing system and a method thereof. More particularly, the present invention relates to a photolithography processing system and a method thereof that is able to detect the presence of particles remaining on a surface of a wafer during the process of forming a pattern mask and then determine a subsequent processing step for the wafer depending on the result of the detection step.

2. Description of the Related Art

In general, a semiconductor device is made by using repetitive and selective process steps, such as photolithography, etching, diffusion, chemical vapor deposition, ion implantation, metal deposition, and the like. One of the more frequently performed process steps is a photolithography process step to form a pattern mask onto the wafer.

A conventional photolithography process will now be described with reference to FIG. 1.

In a conventional photolithography processing system as shown in FIG. 1, a plurality of wafers W mounted on a carrier C are moved from a production line onto a loader 12 and then transported one by one to a desired location by a plurality of robots R1, R2, R3 of a transporter 14, which is installed on one side of the loader 12.

At this time, a first robot R1, positioned adjacent to the loader 12, takes a wafer out of the carrier C and moves it onto a first table T1, which is positioned between the first robot R1 and a second robot R2. The second robot R2 then moves the wafer W placed on the first table T1 through a pre-processing unit 16 where pre-treatment steps are performed prior to a photo-exposure process. The pre-treatment steps performed include depositing a coating liquid onto the surface of the wafer W, adding photoresist to the surface of the wafer W covered with coating liquid, heating and cooling the coating liquid and the photoresist deposited surface of the wafer and removing the remaining photoresist deposited on an edge portion of the wafer W with photo-exposure.

Then, the wafer, having been pre-treated by the aforementioned steps, is transported by the second robot R2 to a second table T2 near a photo-exposure unit 18. Next, a third robot R3, positioned adjacent to the photo-exposure unit 18, transports the wafer to the photo-exposure unit 18 for sequential steps of alignment, photo-exposure and inspection. After inspection, the third robot R3 returns the wafer W to the second table T2.

After having been through a series of processing steps after photo-exposure, the wafer is moved by the second robot R2 to a post-processing unit 20 where a series of post-treatment steps, including developing and cleaning steps, are performed. After the post-treatment steps, the second robot R2 returns the wafer W to the first table T1, which is near the loader 12, for a subsequent unloading step. During the unloading step, the first robot R1 mounts the wafer W onto a requested carrier C.

During the series of processing steps, there may be a number of impure matters, such as particles, remaining on the surface of the wafer W that has been through the series of processing steps for photo-exposure. These impure matters remaining on the wafer surface may generate defects and other faults in the process of the photoresist coating and photo-exposure steps.

As a result, the presence of impure matters increases a re-work rate of photolithography processing steps and decreases productivity. Moreover, the presence of impure matters deteriorates the quality and yield of resultant semiconductor devices.

Moreover, it is possible for the wafer W, transported through the post-processing unit 20 that performs a development step and mounted again onto the carrier C of the loader 12, to have particles remaining on the surface thereof, which become a problem by causing defects in subsequent processing steps.

SUMMARY OF THE INVENTION

In an effort to solve the above-mentioned problems, it is a feature of an embodiment of the present invention to provide a photolithography processing system and method thereof that is able to detect the presence of impure matters, including particles, remaining on a surface of a wafer to which a photo-exposure step will be performed, to provide for the removal of the impure matters from the wafer to prevent defects and faults possible in a series of subsequent processing steps, including photo-exposure, thereby reducing a re-work rate, increasing productivity and improving the quality and yield of semiconductor devices.

In order to provide the aforementioned feature of an embodiment of the present invention, there is provided a photolithography processing system comprising: a table positioned near a loader, where a carrier is positioned, for supporting a wafer that is being transported by a robot; a plurality of illumination tools for illuminating a surface of the wafer positioned on the table; a camera for taking pictures of the surface of the wafer; and a controller for controlling operations of the robot, the plurality of illumination tools and the camera and for detecting the presence of impure matters on the surface of the wafer.

The plurality of illumination tools may be singular or plural lasers, ultraviolet lamps, or a combination of the two. The camera may be made of a charge-coupled device.

The plurality of illumination tools may be provided by first illumination tools positioned laterally at different heights to illuminate the surface of the wafer at various predetermined angles of incidence and a second illumination tool to illuminate the surface of the wafer vertically from above the wafer on the table.

Preferably, the first illumination tools are position to have an angle of incidence ($\theta$) ranging between greater than 0° and less than approximately 70° (i.e., $0° < \theta < 70°$) relative to the surface of the wafer positioned on the table.

In addition, a half-mirror may be positioned between the camera and wafer and apart from the angle of incidence of the plurality of first illumination tools. In an embodiment of the present invention, the second illumination tool is positioned to illuminate the surface of the wafer through the half-mirror. Alternatively, the second illumination tool may be positioned around the camera, without the addition of the half-mirror. In another embodiment of the present invention, the second illumination tool may be a plurality of second illumination tools.

Preferably, the controller additionally controls a luminous intensity and an angle of incidence according to an illumination control signal. More specifically, wherein the illumination tools include the plurality of first illumination tools positioned at varying heights on both sides of the table to allow illumination at varying angles of incidence and the second illumination tool vertically illuminating the surface of the wafer from above the wafer on the table, the controller may include: elevating means to slide up or down the first illumination tools in response to an applied illumination control signal and a luminous intensity unit to control luminous intensity by varying a value of a resistance connected in series with the power source that is connected to the first and second illumination tools in response to other applied illumination control signals.

In an embodiment of the present invention, the table is preferably able to rotate in response to the control signals from the controller, thereby making it possible to rotate the position of the wafer in response to angles of incidence of the first and second illumination tools. In addition, the table may be installed to allow lateral and longitudinal movement.

Another feature of an embodiment of the present invention provides a method of a photolithography processing system including: illuminating a surface of a wafer with first and second illuminating tools; taking pictures of the surface of the wafer with a camera while the surface of the wafer is being illuminated; receiving a signal from the camera in a controller; detecting a presence of particles on the surface of the wafer with the controller; and transporting the wafer to the process-performing or cleaning position according to whether particles are detected on the surface of the wafer.

In an embodiment of the present invention, the illuminating of the surface of the wafer includes: positioning a plurality of first illumination tools at varying lateral heights relative to the table to illuminate the surface of the wafer at predetermined angles of incidence; and positioning the second illumination tool to illuminate the surface of the wafer vertically from above the wafer on the table.

In an embodiment of the present invention, the taking pictures of the surface of the wafer includes: obtaining a first image while the first illumination tools are maintained in an 'on' position and the second illumination tool is maintained in an 'off' position; obtaining a second image while the first illumination tools are maintained in an 'off' position and the second illumination tool is maintained in an 'on' position; and forming a multi-dimensional image by combining the first and second images.

These and other features of the present invention will be readily apparent to those of ordinary skill in the art upon review of the detailed description that follows.

DETAILED DESCRIPTION OF THE INVENTION

Korean Patent Application No. 2001-41473, filed on Jul. 11, 2001, and entitled: "Photolithography Processing System and Method Thereof," is incorporated by reference herein in its entirety.

A photolithography processing system and a method thereof will now be described with reference to accompanying drawings in accordance with the present invention.

Figure 1:
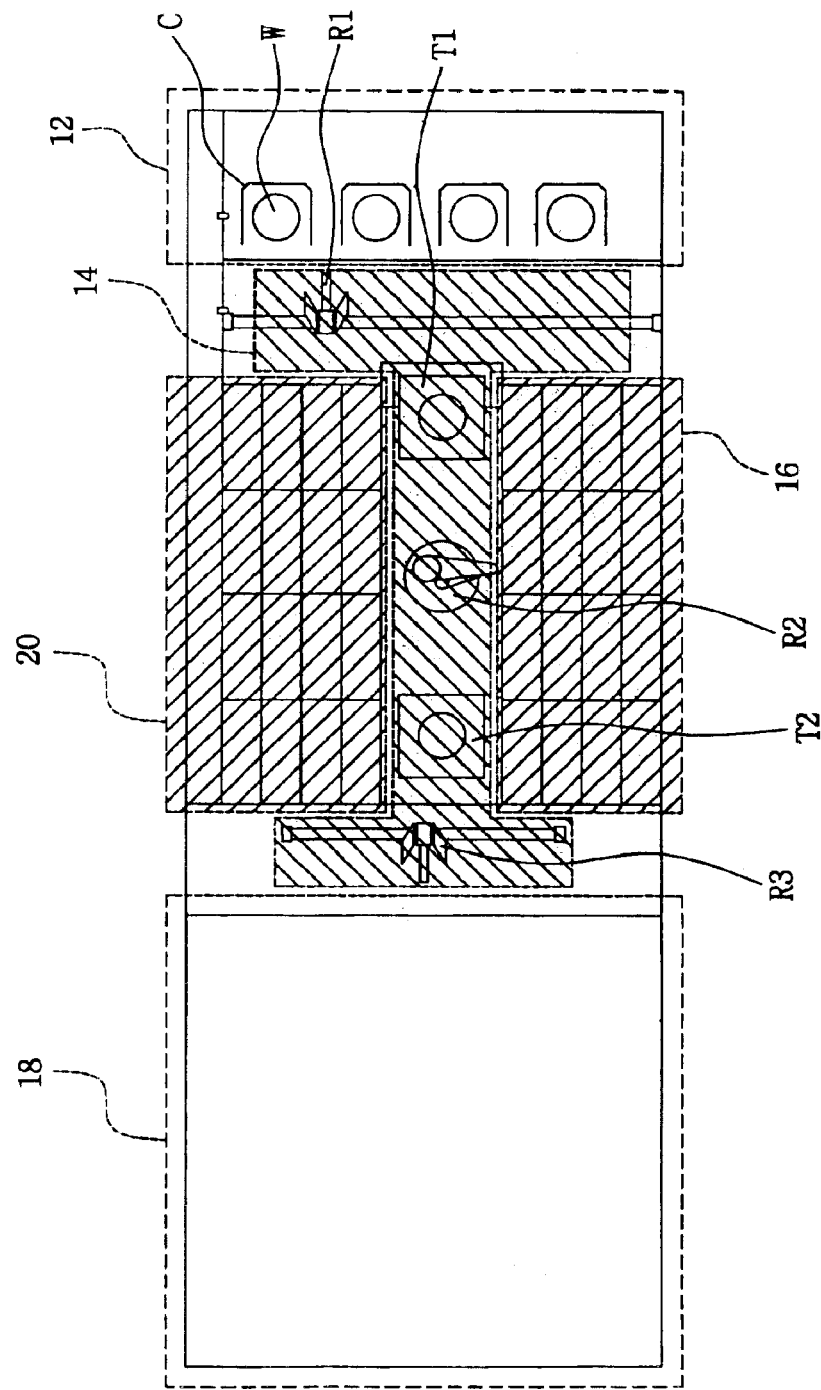
FIG. 1 illustrates a schematic of a structure of a conventional semiconductor device photolithography processing system according to the prior art.
Figure 2:
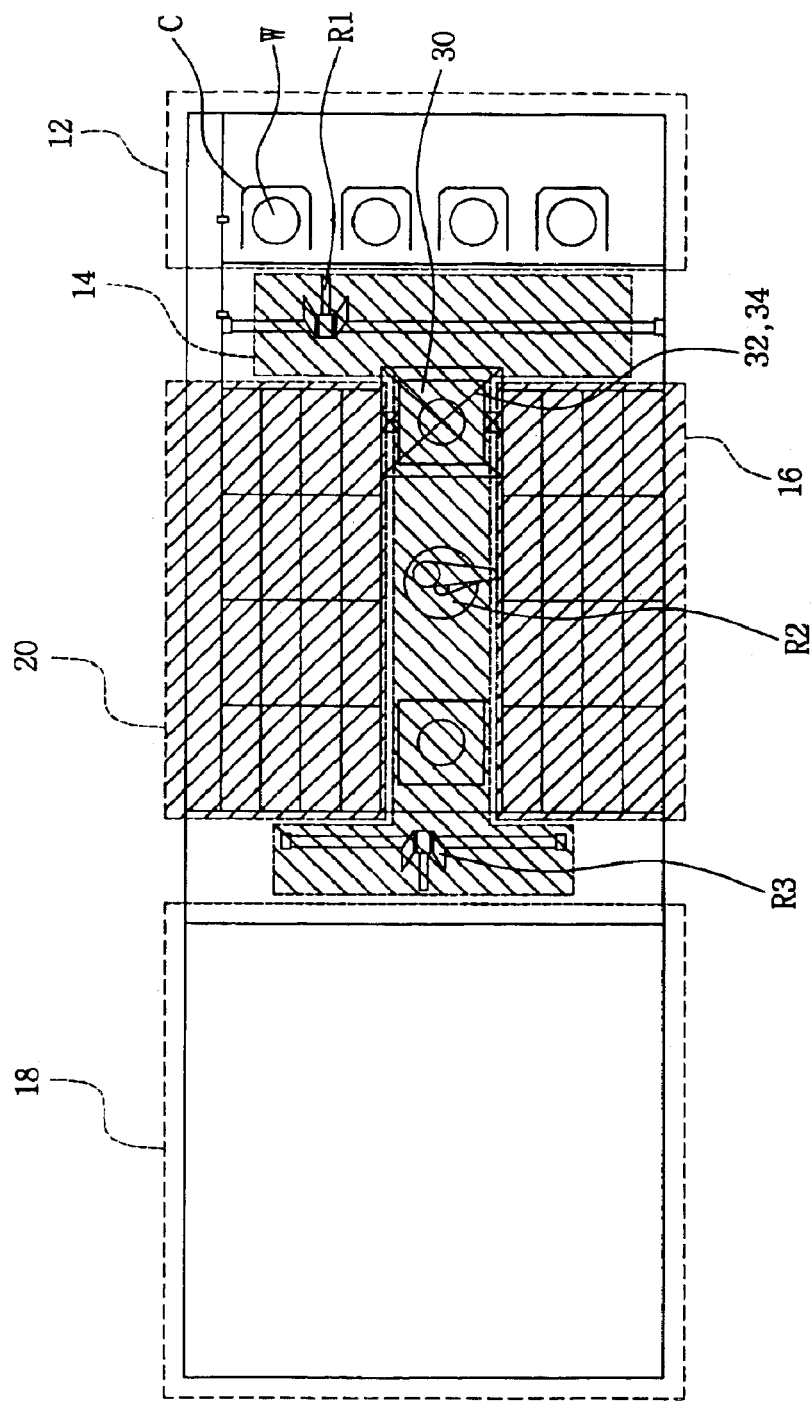
FIG. 2 illustrates a schematic of a structure of a semiconductor device photolithography processing system in accordance with an embodiment of the present invention.

In a semiconductor device photolithography processing system of the present invention, as shown in FIG. 2, a plurality of wafers W mounted on a carrier C are moved from a production line onto a loader 12 and then transported one by one to a desired location by a plurality of robots (R1, R2, R3) to a transmission unit 14, which is installed on one side of the loader 12.

In the transmission unit 14 near the loader 12, there is provided a table 30 for temporarily supporting the wafer W. The table 30 supports the wafer when the wafer W is moved from the carrier C by a first robot R1 for further operations, during inspection, and when the wafer W is unloaded by a second robot R2 after completion of pre-processing steps before it is placed into a predetermined carrier C of the loader 12. During inspection, the wafer W on the table 30 will be examined for impure matters, such as particles, on a surface thereof.

Figure 3:
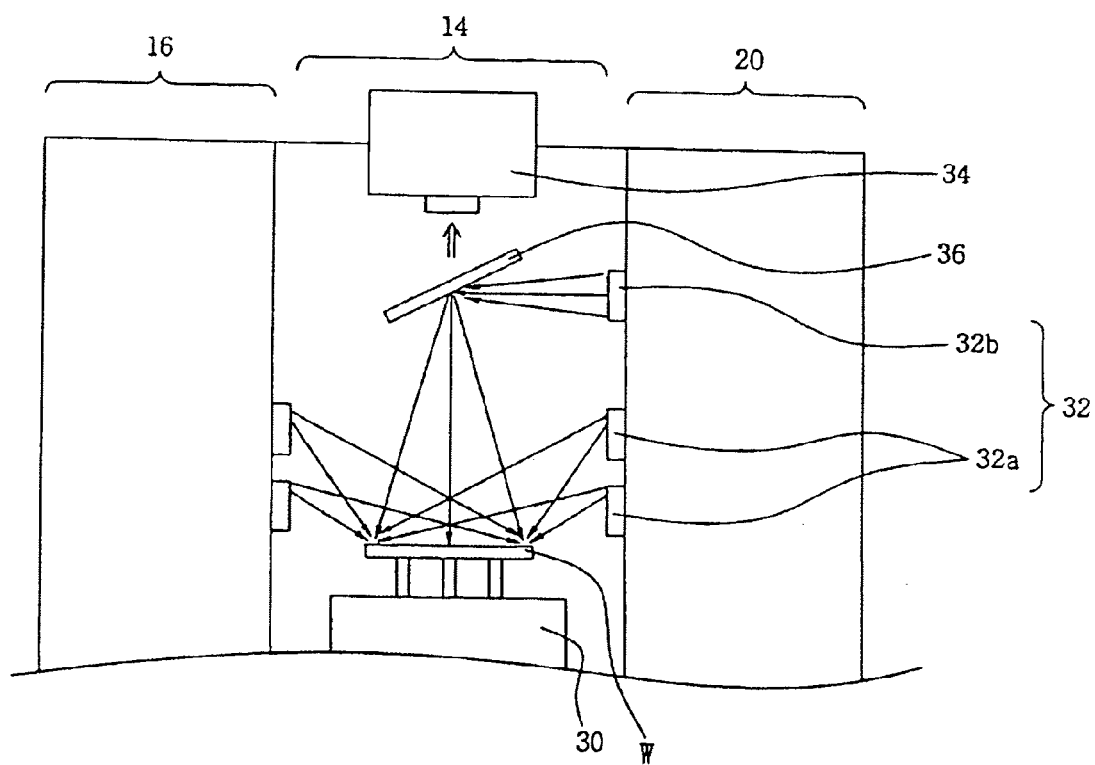
FIG. 3 illustrates a side view schematic of a structure of a particle inspecting unit as shown in FIG. 2.

As shown in FIG. 3, a plurality of illumination tools 32 are installed on both sides of the table 30 to illuminate light directly onto the surface of the wafer W positioned on the table 30. A camera 34 is installed at a predetermined position relative to the table 30 to take pictures of the surface of the illuminated wafer W on the table 30.

In the above-described structure, a controller (not shown) controls the robots R1, R2, R3, the illumination tools 32, and the camera 34. A wafer surface state showing signal obtained by the camera 34 is transmitted to the controller to detect the presence of particles on the surface of the wafer W.

Referring to FIG. 3, the illumination tools 32 may be made of singular or plural lasers, ultraviolet lamps, or a combination of the two. The camera 34 may be made of a charge-coupled device.

Preferably, the illumination tools 32 are a plurality of first illumination tools 32a and a second illumination tool 32b. Preferably, the first illumination tools 32a are positioned at different heights on both sides of the table 30 to illuminate the surface of wafer W at various predetermined angles of incidence. Preferably, the second illumination tool 32b is positioned to illuminate the surface of the wafer W vertically from above.

Preferably, the first illumination tools 32a are constructed within an angle of incidence ($\theta$) ranging from between greater than 0° and less than approximately 70° (i.e., 0°<$\theta$<70°) relative to the surface of the wafer positioned on the table 30. The angle of incidence range of the first illumination tools 32a is set in cooperation with the second illumination tool 32b to prevent an occurrence of a dark shadow in the circuit pattern or pattern mask formed on the surface of the wafer during the photolithography process.

Additionally, a half-mirror 36 may be provided at a predetermined position apart from the first illumination tools 32a and positioned between the wafer W and the camera 34. The camera 34 is positioned vertically above the wafer. As shown in FIG. 3, the second illumination tool 32b may be installed at a predetermined lateral position apart from the table 30 for vertical illumination onto the wafer W through the aforementioned half-mirror 36.

Figure 4:
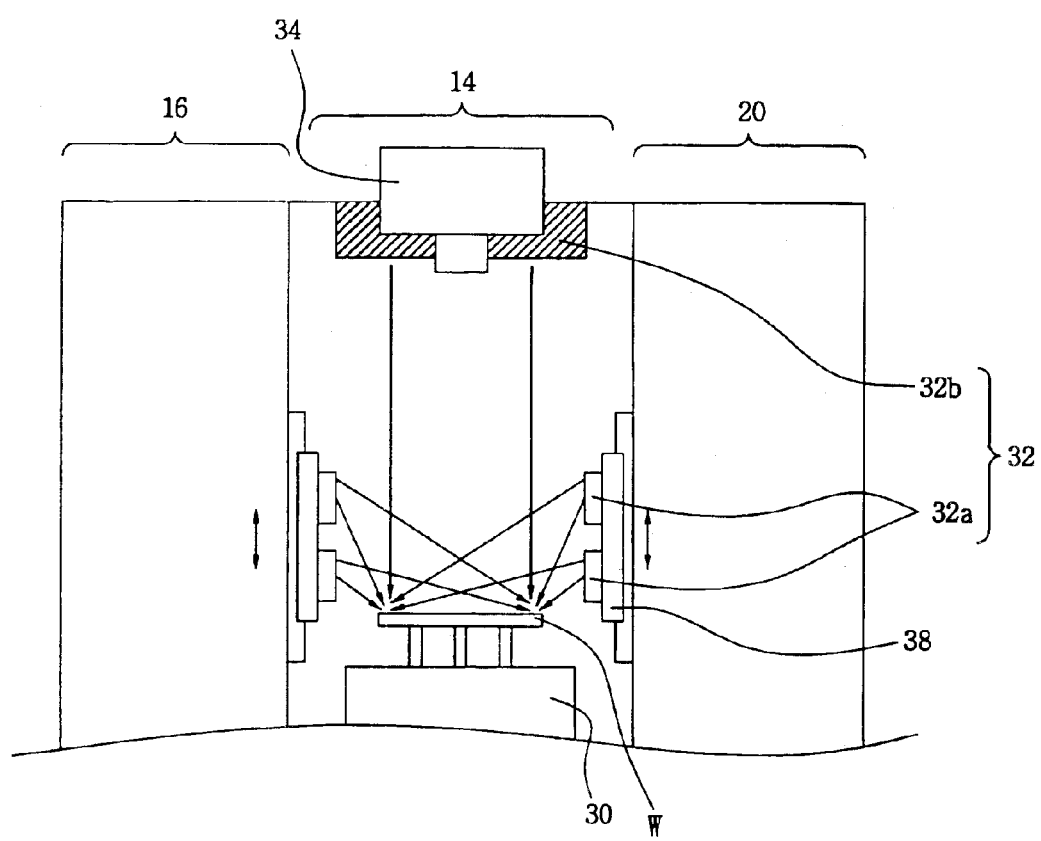
FIG. 4 illustrates a side view schematic of an alternate embodiment of a particle inspecting unit according to the present invention.

Alternatively, as shown in FIG. 4, a plurality of second illumination tools 32b may be positioned vertically above the surface of wafer W and positioned around the camera 34.

Additionally, the table 30, on which the wafer is placed, may be made to rotate the wafer as the positions of the illumination tools 32 are limited in their directions from which to illuminate the circuit patterns formed on the surface of wafer W. Moreover, the table 30 may be provided to allow lateral and longitudinal movement as the focus of the camera 34 is restricted to a specific portion of the wafer W.

On the other hand, a controller (only partially shown) may be installed as part of the illumination tools 32 for controlling the luminous intensity and angle of incidence according to an applied illumination control signal. Preferably, the controller includes: elevating means 38 to slide the first illumination tools 32a up or down in response to an illumination control signal applied from the controller and a luminous intensity controlling unit (not shown) for controlling the luminous intensity by varying a value of a resistance connected in series with the power source that is connected to the first and second illumination tools 32a, 32b in response to other applied illumination control signals. The controller also controls operations of the robots R1, R2 and R3.

Accordingly, the illumination tools 32 illuminate the surface of the wafer on the table 30 without leaving any darkness caused by a circuit pattern formed on the surface of the wafer or a pattern mask resulting from the photolithography process. At this time, the camera 34 takes a picture of the surface of the wafer to transmit the relevant signal to the controller.

Then, the controller that has received the picture signal of the surface state of the wafer from the camera 34 detects the presence of particles remaining on the surface of the wafer based on a comparison with preset data. The controller then determines where to move the wafer W based on the results of the detection of particles.

Preferably, the illumination tools 32 are arranged with the first illumination tools 32a forming various predetermined angles of incidence to the surface of the wafer and the second illumination tools 32b illuminating the wafer surface vertically from above the wafer. Preferably, a first image is obtained by taking a picture of the lateral shape of the circuit pattern or pattern mask with the first illumination tools 32a turned 'on' while the second illumination tool is maintained in an 'off' position. Next, a second image is obtained by taking a picture of the top shape of the circuit pattern or pattern mask while the first and second illumination tools 32a, 32b are maintained in an 'off' and 'on' position, respectively. When the first and second images are combined to form a multi-dimensional image, it is relatively easy to detect the presence of particles remaining on the surface of the wafer.

Furthermore, the first illumination tools 32a may be slid up or down to prevent any interference on the lateral shape of the circuit pattern or pattern mask. In other words, in a preferred embodiment of the present invention, the first illumination tools 32a are able to slide up or down in response to the width and depth of the grooves of circuit pattern or pattern mask. The angle of incidence of the first illumination tools 32a is varied by the up and down sliding motion. The picture signal, or illumination signal, from the camera, which is transmitted to the controller, controls the luminous intensity controlling unit and the elevating means to slide the illumination tools up or down.

As described above, there are advantages in the photolithography processing system of the present invention in that it is possible to detect the presence of impure matters, including particles, on the surface of a wafer in the loading and unloading processes for photo-exposure, remove the impure matters, if any, and perform a series of subsequent operations or re-works relevant to the photo-exposure step, so that the wafer inspecting step prior to photo-exposure can effectively decrease the re-work rate, increase productivity and improve the quality and yield of resultant semiconductor devices.

Preferred embodiments of the present invention have been disclosed herein and, although specific terms are employed, they are used in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A method of a photolithography processing system, comprising:

illuminating a surface of a wafer supported by a table with first illumination tools and a second illumination tool by positioning the first illumination tools at varying lateral heights relative to the table to illuminate the surface of the wafer at various predetermined angles of incidence and positioning the second illumination tool to illuminate the surface of the wafer vertically from above the wafer on the table;

taking pictures of the surface of the wafer with a camera while the surface of the wafer is being illuminated;

receiving a signal from the camera in a controller;

detecting a presence of particles on the surface of the wafer with the controller; and transporting the wafer to the process-performing or cleaning position according to whether particles are detected on the surface of the wafer.

2. The method of a photolithography processing system as claimed in claim 1, wherein the taking of pictures of the surface of the wafer comprises:

obtaining a first image while the first illumination tools are maintained in an 'on' position and the second illumination tool is maintained in an 'off' position;

obtaining a second image while the first illumination tools are maintained in an 'off' position and the second illumination tool is maintained in an 'on' position; and forming a multi-dimensional image by combining the first and second images.

3. The method of a photolithography processing system as claimed in claim 1, wherein positioning the first illumination tools at varying lateral heights relative to the table to illuminate the surface of the wafer at various predetermined angles of incidence comprises positioning the first illumination tools to have an angle of incidence varying between 0° and approximately 70°.

4. The method of a photolithography processing system as claimed in claim 1, further comprising controlling the angle of incidence of the first illumination tools in accordance with an illumination control signal.

5. The method of a photolithography processing system as claimed in claim 1, further comprising altering the lateral height of the first illumination tools in accordance with an illumination control signal.

6. The method of a photolithography processing system as claimed in claim 1, wherein the second illumination tool is positioned around the camera.

7. The method of a photolithography processing system as claimed in claim 1, wherein the first illumination tools are positioned on both sides of the table to allow various changes in height for illuminating at an angle of incidence; and the second illumination tool vertically illuminates the surface of the wafer from the top of the table.

8. The method of a photolithography processing system as claimed in claim 1, further comprising rotating the table in response to a control signal to thereby rotate a position of the wafer in response to angles of incidence of the first illumination tools and the second illumination tool.

* * * * *